United States Patent

Burrous et al.

[11] Patent Number: 5,769,385
[45] Date of Patent: Jun. 23, 1998

[54] TUBING CLAMPS FOR BLOOD SEPARATING APPARATUS

[75] Inventors: Dale Burrous, Gilcrest; Mark T. Patton, Denver, both of Colo.

[73] Assignee: Medtronic Electromedics, Inc., Parker, Colo.

[21] Appl. No.: 786,028

[22] Filed: Jan. 21, 1997

Related U.S. Application Data

[60] Provisional application No. 60/010,922 Jan. 31, 1996.

[51] Int. Cl.[6] ..................................................... F16K 7/06
[52] U.S. Cl. .................................. 251/7; 251/77; 251/251
[58] Field of Search .................................... 251/4, 7, 251, 251/77

[56] References Cited

U.S. PATENT DOCUMENTS

| 2,732,166 | 1/1956 | Rayner, Jr. ........................... 251/251 X |
| 3,550,619 | 12/1970 | Halary ..................................... 251/7 X |
| 3,913,621 | 10/1975 | Damratowski ...................... 251/251 X |
| 4,086,924 | 5/1978 | Latham, Jr. . |
| 4,354,984 | 10/1982 | Riehordsay et al. ..................... 251/7 X |
| 4,653,719 | 3/1987 | Colrera et al. .............................. 251/7 |
| 4,668,214 | 5/1987 | Reeder . |
| 4,895,341 | 1/1990 | Brown et al. .......................... 251/77 X |
| 5,311,908 | 5/1994 | Parone et al. ............................ 251/7 X |

*Primary Examiner*—John Fox
*Attorney, Agent, or Firm*—Ancel W. Lewis, Jr.

[57] ABSTRACT

A pinch clamp finding a primary use in an autotransfusion machine includes a hollow clamp head having a closed upper end and an open lower end reciprocally receiving a piston. A lateral groove is established in the clamp head so that a deformable tube can be received in the clamp head passing through the hollow interior thereof. The piston is reciprocally moved within the clamp head so as to selectively pinch the tube between the piston head and the closed end of the clamp head. The piston is positively reciprocated by cam followers on a piston rod with the cam followers riding in closed cam tracks in adjacent cam wheels on opposite sides of the piston. The cam wheels are mounted on a crankshaft which is selectively driven by power means.

14 Claims, 6 Drawing Sheets

Fig. 10

TUBING CLAMPS FOR BLOOD SEPARATING APPARATUS

This application claims the benefit of U.S. Provisional Application No. 60/010,922, filed 31 Jan., 1996.

BACKGROUND OF THE INVENTION

1. Field of the Invention

This invention relates generally to equipment for blood transfusions or reinfusions and more particularly to a system for selectively occluding the flow of fluids through tubes in an autotransfusion machine.

2. Description of the Prior Art

Whole human blood includes at least three types of specialized cells. These are the red blood cells, white blood cells and platelets. All of these cells are suspended in plasma, a complex aqueous solution of proteins and other chemicals.

When removing blood from a donor for homologous transfusion, for reinfusion or when obtaining blood for plasmapheresis, and/or salvaging blood from a body cavity or a wound site, it is important to remove the undesirable elements from the blood before reinfusing or transfusing the blood into a patient. The undesirable elements that must be removed include plasma, activated clotting factors and/or by-products of coagulation, drugs, cellular debris, platelets and leukocytes, otherwise referred to as white blood cells. The only element of the blood which remains after the removal of the undesirable elements are the red blood cells, which are the desirable element for reinfusion or transfusion.

Numerous systems have been developed for cleaning whole blood by removing the undesirable elements, examples of which are disclosed in U.S. Pat. No. 4,086,924 issued to Latham, Jr., and U.S. Pat. No. 4,668,214 issued to Reeder which is of common ownership with the present application. These systems include means for removing the blood from a patient, adding an anticoagulant to the blood, separating the various components of the blood, usually in a centrifugal separator, washing the desirable red blood cell component which is retained in the separator with a saline solution, and then reinfusing the clean red blood cells into the patient from whom the blood was drawn or transfusing the blood into a donor patient.

The separation and washing process, as mentioned above, is normally accomplished in a centrifugal separator commonly referred to as an autotransfusion machine, wherein the whole blood, including the anticoagulant, is introduced through a central column of a rotating centrifugal separator bowl so that the blood will flow to the outer edge of the bowl and subsequently upwardly along a circumferential wall of the bowl until the lighter elements are discharged through an outlet provided near the top of the bowl. The red blood cells being the heaviest component of whole blood remain in the bowl for the longest period of time so that the lighter, undesirable elements are discharged before the red blood cells fill the separating bowl. Once the bowl is substantially full of red blood cells, the cells have become compacted against the circumferential wall of the bowl and portions of the plasma remain trapped in the interstitial spaces between the red blood cells. In order to remove the plasma from the spaces between the red blood cells, it has been common practice to pass a saline solution through the centrifugal separator to wash the plasma out of the interstitial spaces between the cells.

In moving blood or its components or saline wash solutions to and from the centrifugal separator bowl, a plurality of transfer hoses or tubes are necessary. In order to selectively control the flow of fluid through the hoses or tubes, pinch clamps are utilized to laterally compress the flexible and deformable tubes to occlude the flow of fluid therethrough. In conventional autotransfusion machines, pinch clamps typically include an outer cylindrical housing having a closed upper end and an open lower end in which a piston is slidably positioned. A transverse channel passes through the cylindrical housing to receive the tube upon which the clamp is operative, with the channel being positioned adjacent the closed end of the housing. The piston upon activation is advanced so as to pinch the tube between the piston and the closed end of the housing at selected times. The pistons are typically power driven into a pinching relationship with the tube but allowed to drop by gravity when nonoperative.

In machines such as autotransfusion machines where the control of fluid through a tube is critical, it would be desirable to have a clamping system that was positively activated in both the pinching and non-pinching conditions, and it is to address this concern that the present invention has been developed.

SUMMARY OF THE INVENTION

The present invention concerns an improved pinch clamp adapted to selectively occlude the flow of fluid through a deformable tube. The clamp includes a hollow clamp head having one closed end and an opposite open end that reciprocally receives a piston. A transverse channel passes through the clamp head adjacent the closed end to receive the tube on which the clamp is operable. The piston rod is movable within the clamp head to pinch the tube between the piston and the closed end of the clamp head.

A positive controlled movement of the piston is effected by a crankshaft having at least one cam wheel thereon with a cam track formed in at least one face of the wheel. A cam follower in the form of a laterally protruding pin on the piston is received in the cam track such that rotative movement of the crankshaft and the associated cam wheel selectively controls the reciprocating movement of the connected piston head such that an associated tube can be positively pinched off or left open depending upon the rotative position of the crankshaft.

A plurality of the pinch clamps are disclosed in a system for selectively occluding the flow of fluid through a plurality of tubes such as are found in an autotransfusion machine. The crankshaft includes a plurality of spaced cam wheels having cam tracks in at least one face thereof adapted to receive and guide a transverse cam follower in an associated piston. The various tubes can thereby be pinched off or left open in any desirable sequence depending upon the relative relationships of the cam tracks associated with the respective pinch clamps and the rotative movement of the crankshaft.

Other aspects, features and details of the present invention can be more completely understood by reference to the following detailed description of a preferred embodiment, taken in conjunction with the drawings and from the appended claims.

DESCRIPTION OF THE PREFERRED EMBODIMENT

Figure 1:
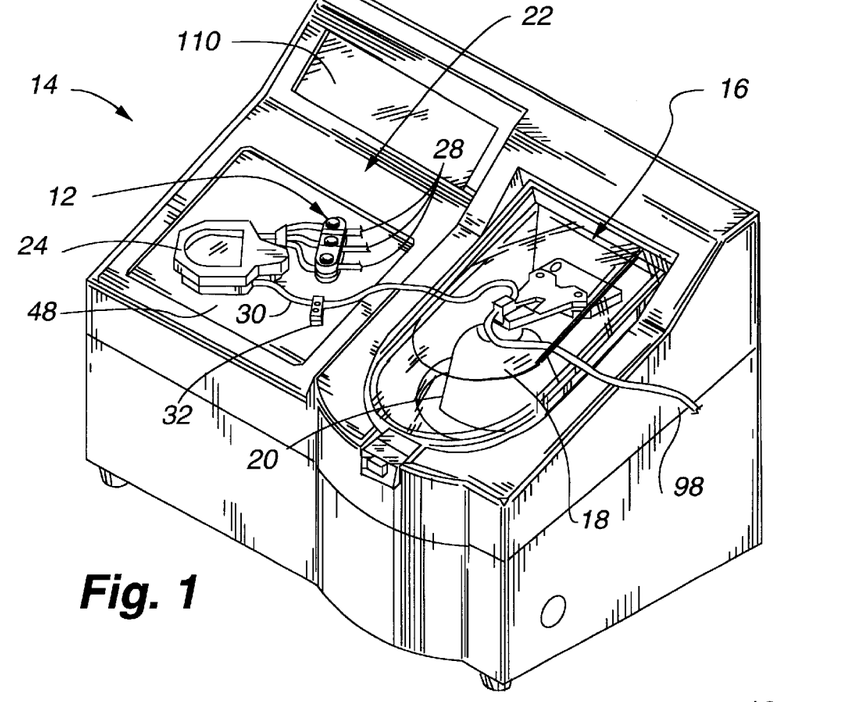
FIG. 1 is an isometric view of an autotransfusion machine incorporating the pinch clamp of the present invention.
Figure 2:
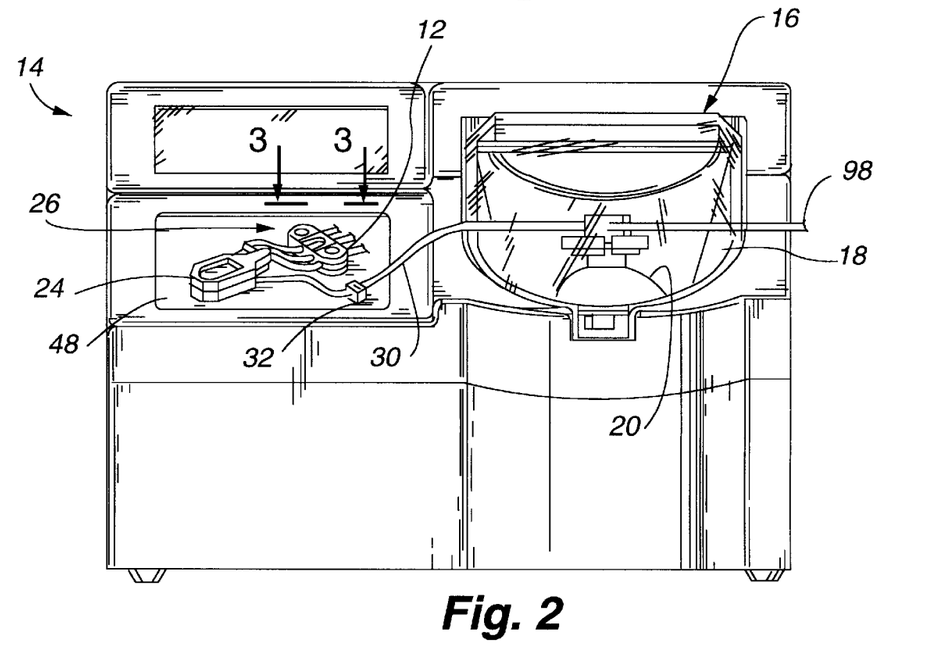
FIG. 2 is a front elevation of the autotransfusion machine shown in FIG. 1.

The pinch clamp 12 of the present invention finds one preferred use in an autotransfusion machine 14 used to salvage blood from a body cavity or a wound site during surgical procedures. When salvaging blood, it is important to remove the undesirable elements from the blood so as to condition the blood for reinfusion or transfusion. A somewhat typical autotransfusion machine 14 is shown in some detail in FIGS. 1 and 2. The machine can be seen to include chamber 16 on the right side having a removable cover 18 providing access to a conventional centrifugal separator bowl 20 positioned in the chamber. Separator bowls for use in autotransfusion machines are relatively common and a detailed description thereof is not felt necessary to an understanding of the present invention. Suffice it to say that the separator bowl is mounted on a rotating platform (not seen). When blood is pumped into the rotating separator bowl, the heavier red blood cell component of the blood remains near the bottom of the bowl while the remaining undesirables such as plasma, activating clotting factors and/or byproducts of coagulation, drugs, cellular debris, platelets and white blood cells are removed through the top of the bowl. A further understanding of the operation of the separator bowl will be set forth hereafter with an explanation of the pinch clamp 12 of the present invention.

On the left side 22 of the autotransfusion machine 14, a fluid pump 24, which can be a peristaltic pump, is positioned on the top of the machine housing adjacent to a bank 26 of pinch clamps 12A, 12B and 12C which receive and are operative upon associated flexible and laterally deformable tubes 28A, 28B and 28C respectively. The tubes are in turn connected to various sources or supply reservoirs which also will be explained later with the operation of the pinch clamps.

Figure 3:
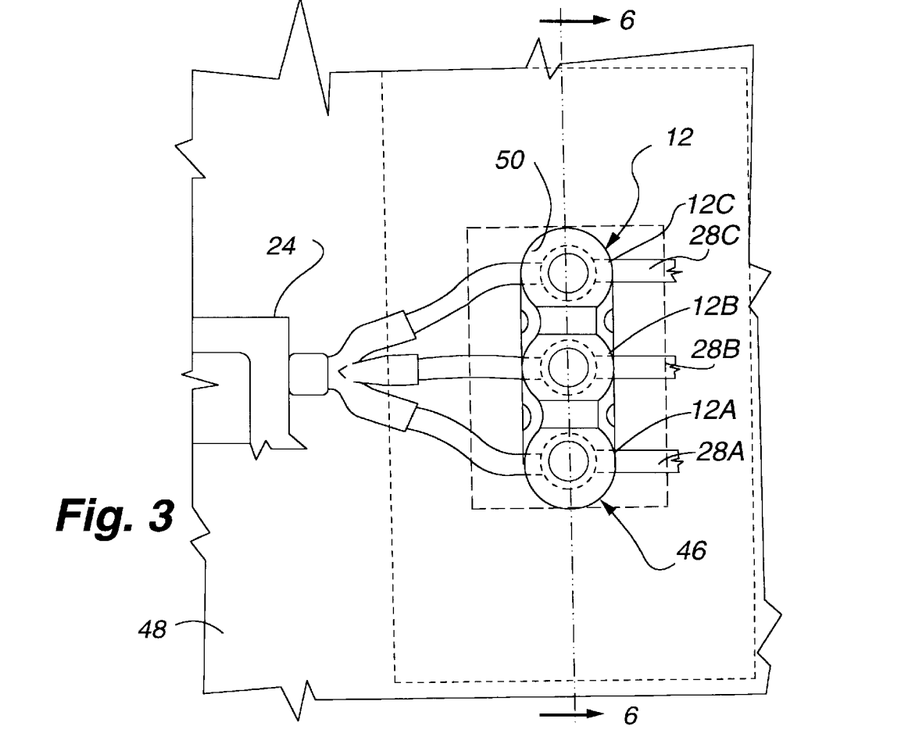
FIG. 3 is a fragmentary enlarged section taken along line 3—3 of FIG. 2.
Figure 4:
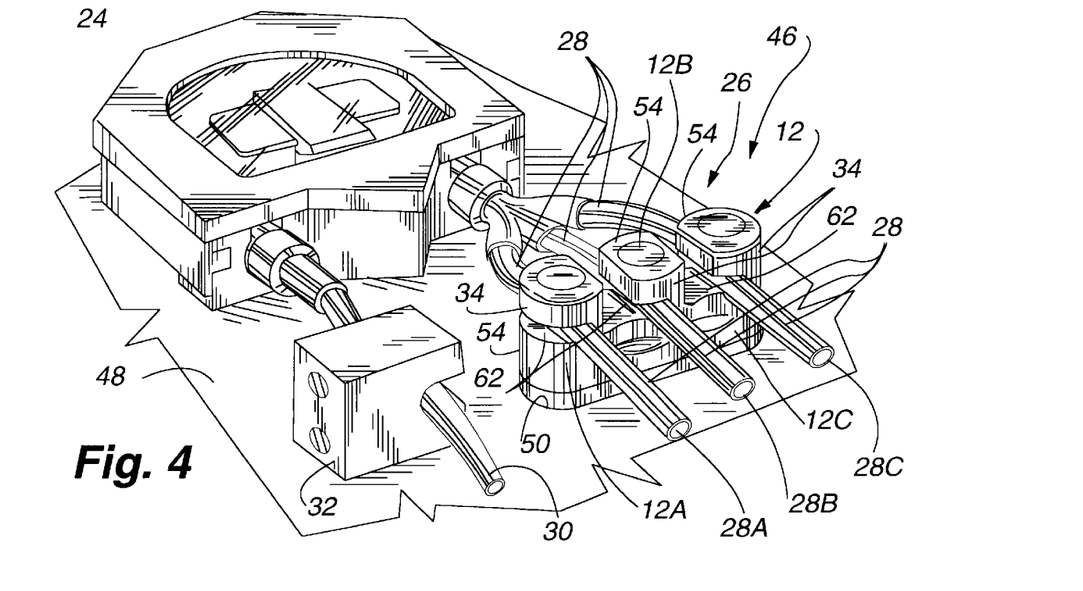
FIG. 4 is a further enlarged fragmentary isometric showing the pinch clamp of the present invention incorporated into the autotransfusion machine.

FIGS. 3 and 4 are enlarged views showing in slightly more detail the bank 26 of pinch clamps of the present invention and the fluid pump 24 to which they are operatively connected through the respective tubes 28 as well as a tube 30 connecting the fluid pump with the separator bowl 20. The tube 30 passes through a bubble detector 32 whose operation will not be explained herein as it is not felt relevant to an understanding of the present invention.

With more particular reference to FIGS. 5 through 9, the pinch clamp 12 of the present invention as mentioned previously is shown as a part of a bank 26 of such clamps as they are found in the autotransfusion machine 14. Referencing first FIG. 5, each pinch clamp 12 can be seen to include a hollow clamp head 34, a clamping element in the form of a piston 36 reciprocally moveable within the clamp head 34, a cam follower pin 38 carried by the piston and a pair of cam wheels 40 having cam tracks 42 for receiving the cam followers 38 with the cam wheels being mounted on a crankshaft 44.

For purposes of the present disclosure, the clamp head 34 associated with an individual pinch clamp 12 forms part of an integrated unit 46 having three such clamp heads in aligned relationship. The clamp head unit 46 is adapted to be secured to the housing 48 of the autotransfusion machine so as to protrude upwardly through an elongated hole 50 formed in the housing. The clamp head unit is secured in place with suitable fasteners 52 so that the clamp heads 34 project upwardly from the top surface of the autotransfusion machine housing as shown clearly in FIGS. 1 through 4.

Each clamp head 34 comprises a substantially cylindrical hollow body 54 having a closed upper end 56 and an open bottom end 58. The clamp head thereby defines a chamber 60 therewithin that opens downwardly to reciprocally receive an associated piston 36. A horizontal transverse groove 62 is formed in a side of the clamp head housing to removably receive a flexible, deformable tube 28 with the groove 62 establishing communication with the internal chamber 60.

Figure 5:
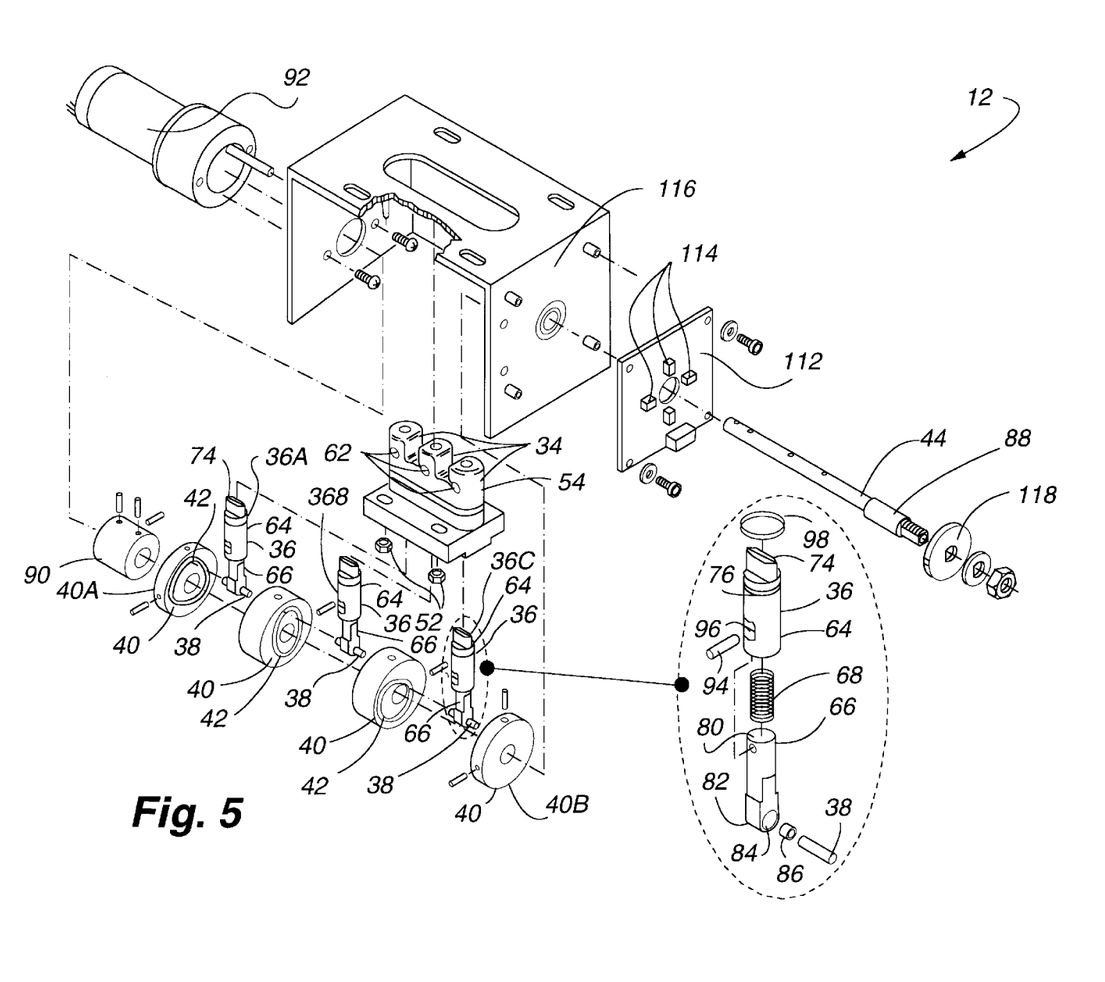
FIG. 5 is an exploded isometric with parts removed for clarity showing the components of the pinch clamp in relation to selected parts of the autotransfusion machine.
Figure 6:
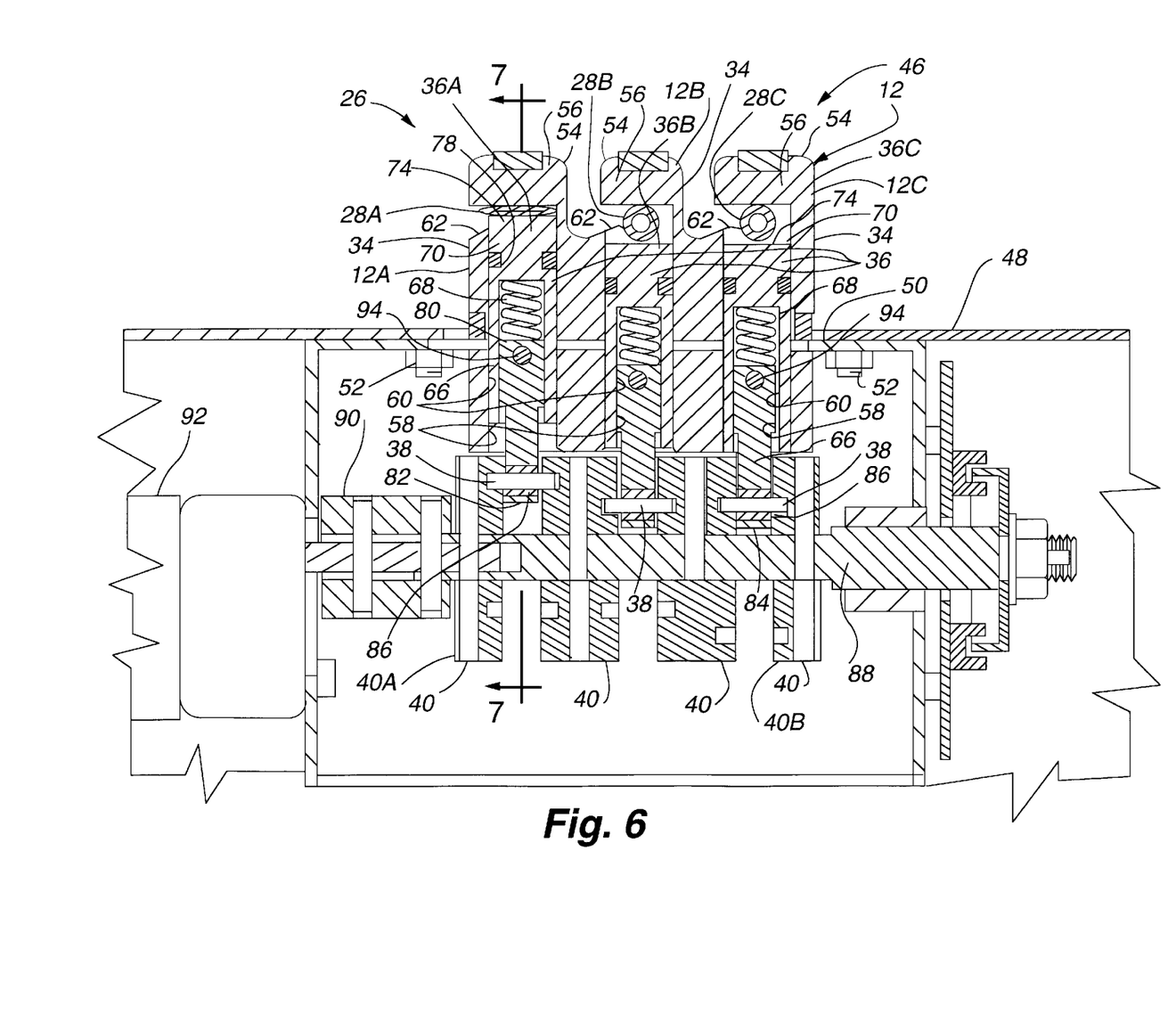
FIG. 6 is a fragmentary section taken along line 6—6 of FIG. 3.
Figure 7:
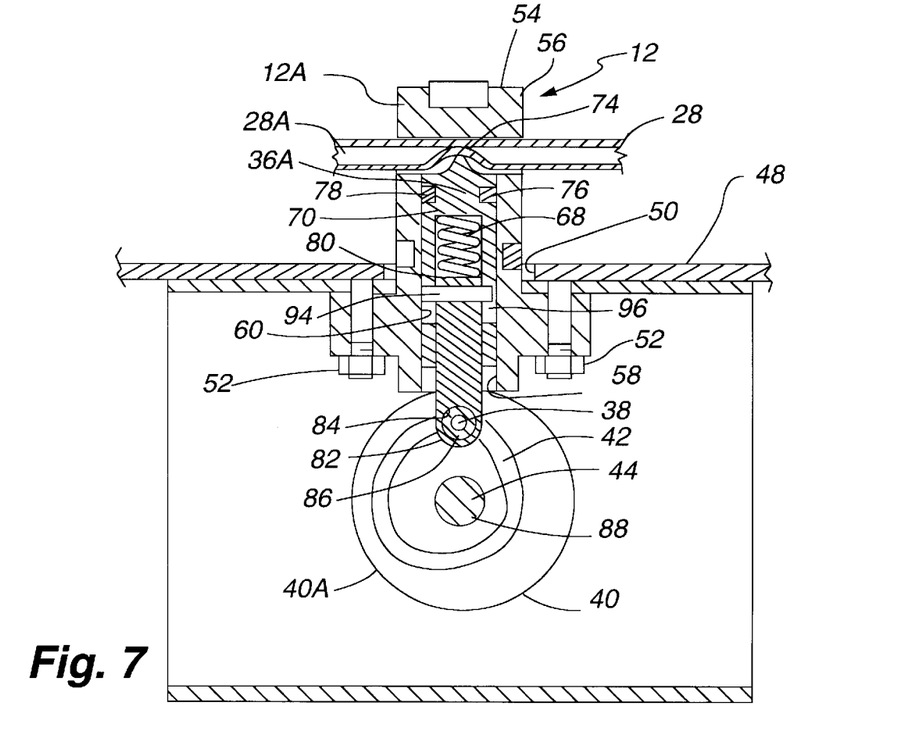
FIG. 7 is a section taken along line 7—7 of FIG. 6.

The piston as probably best seen in FIGS. 5, 6 and 7 includes a piston head 64, a piston rod 66, the cam follower pin 38 and a compression spring 68 disposed between the piston rod and the piston head. The piston head 64 is a hollow cylindrical element having a closed upper end 70 and an open bottom end 72 which receives the piston rod 66. The top of the piston head has an upwardly projecting pinch bar 74 which is adapted to engage a deformable tube 28 to occlude the flow of fluid through the tube in a manner to be described later. The piston head also has an annular groove 76 adjacent to its upper end for receiving a sealing ring 78 that guides the reciprocating movement of the piston head within the clamp head.

The piston rod 66 is an elongated element having an upper end 80 of substantially solid cylindrical configuration and a rounded lower end 82 having a transverse passage 84 therethrough. The transverse passage 84 seats a compression ring 86 that frictionally grips and retains the cam follower pin 38 as best seen in FIG. 6. The cam follower pin projects laterally from either side of the piston rod.

The compression spring 68 is positioned and retained within the hollow interior of the piston head 64 and compressively engages the upper end of the piston rod 66 so as to yieldingly resist upward sliding movement of the piston rod within the piston head. The spring 68, as will be appreciated with the description that follows, thereby allows the pinch bar 74 on the piston head to move smoothly into pinching engagement with a deformable tube 28 even though the piston rod itself is moving very positively and somewhat abruptly.

The cam follower pin 38 on the lower end of the piston rod 66 is adapted to ride within and be guided by opposing cam tracks 42 established in the form of closed loop grooves in the opposing faces of adjacent cam wheels 40 between which the piston 36 is disposed.

The piston 36 is positioned vertically above a drive or crankshaft 88 on which the cam wheels 40 are mounted and keyed for unitary rotation therewith. While each cam track 42 surrounds the axis of rotation of its associated cam wheel, the cam tracks associated with a given piston 36 are identical and angularly aligned. Since they move in unison on the same crankshaft, the cam tracks cause the associated piston to reciprocate linearly and vertically above the crankshaft. The crankshaft itself is keyed in a bearing 90 that is operatively connected to a drive motor 92 mounted within the autotransfusion machine 14 to selectively rotate the crankshaft.

As will be appreciated by reference to FIGS. 5 and 6, there are four cam wheels 40 mounted on the crankshaft 88 with a piston 36 disposed between pairs of cam wheels. Accordingly, there are three pistons, two outer-most cam wheels 40A and two inner-most cam wheels 40B. The outermost cam wheels 40A have a cam track 42 in only one face while the inner-most can wheels 40B have cam tracks in both faces. As mentioned previously, the cam tracks in opposing faces of adjacent cam wheels are identical in configuration and aligned with each other so as to uniformly and positively raise and lower the piston whose cam follower 38 is received in those tracks. As can be appreciated by reference to FIGS. 5 and 6, the cam tracks associated with each piston are angularly displaced from and/or of a different configuration than the cam tracks associated with the other pistons so that the pistons 36 will move up and down within their clamp heads 34 in predetermined sequence and cycles that are determined by the associated cam tracks and the desired operation of the autotransfusion machine.

As mentioned previously, each clamp head 34 has a transverse groove 62 formed in a side thereof with the groove communicating with the hollow interior chamber 60 of the clamp head. The transverse groove is adapted to removably receive an associated deformable tube 28 so that the tube passes transversely across the hollow interior of the clamp head and in vertical alignment with the associated piston 36. The groove 62 in each clamp head is adjacent to the closed upper end 56 of the clamp head so that upward movement of an associated piston can engage the tube and pinch it against the closed upper end of the clamp head to deform the tube and occlude the flow of fluid through the tube. In order to assure a positive occlusion of the tube, the pinch bar 74 on the top of each piston head is positioned to extend perpendicularly relative to the groove that receives the tube and thus perpendicularly to the tube itself. To retain this alignment, an alignment pin 94 is fixed in the upper end of the piston rod 66 and protrudes through an elongated vertical slot 96 in the side wall of a piston head 64 to retain angular alignment between the piston rod and the piston head. Of course, the piston rods themselves are retained in a predetermined angular orientation due to the operative relationship between the cam follower pin 38 on the piston rod and the cam wheels 40.

Figure 8:
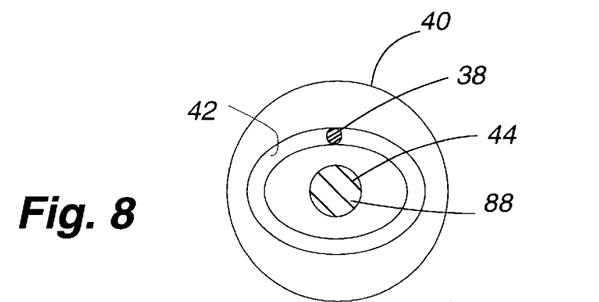
FIG. 8 is a section taken substantially along line 8—8 of FIG. 6.
Figure 9:
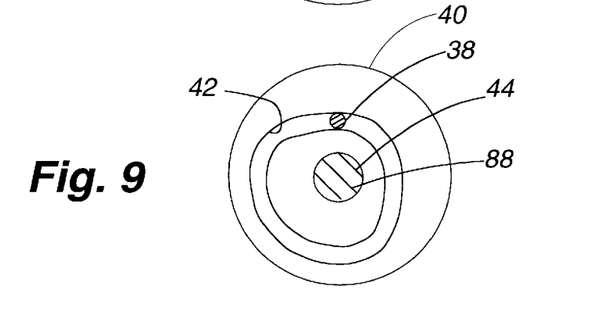
FIG. 9 is a section taken substantially along line 9—9 of FIG. 6.

With reference to FIGS. 7, 8 and 9, it will be seen that, as mentioned previously, the pairs of cam tracks 42 associated with each piston 36 are angularly displaced and/or of different configuration relative to the pairs of cam tracks associated with the other pistons. In fact, the identical cam tracks associated with the middle piston 36B are of a different configuration than the identical cam tracks associated with the outer-most pistons 36A and 36C. Further, the cam tracks associated with the outer-most pistons 36A and 36C are eccentrically disposed relative to the axis of rotation of the cam wheels while the cam tracks associated with the middle piston 36B are not eccentric and are of substantially elliptical configuration.

The sequence of operation of the pistons 36 can be determined by the configuration of the associated cam tracks 42 and the relationship of the cam tracks of adjacent pistons. For purposes of the present disclosure, however, and in accordance with the use of the pinch clamps 12 in an autotransfusion machine, a brief description of the operation of such a machine will be given.

Figure 10:
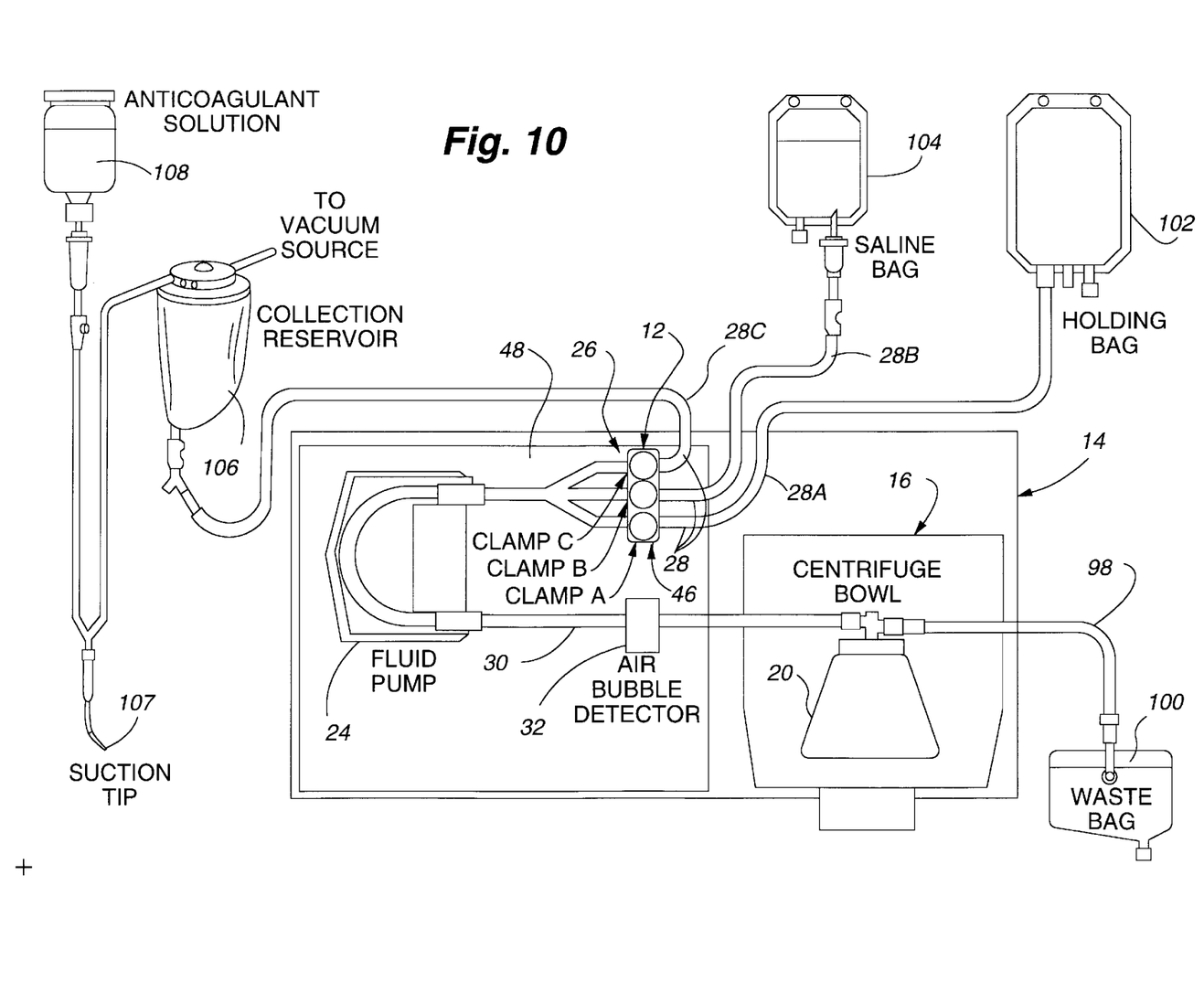
FIG. 10 is a diagrammatic illustration of an autotransfusion machine incorporating the pinch clamps of the present invention and associated containers utilized in the processing of blood.

Referring to FIG. 10, a diagrammatic representation of the autotransfusion machine 14 and associated containers and equipment is shown. The separator bowl 20 is shown mounted in the machine and connected via a first tube 98 to a waste bag 100. The separator bowl is connected via the second tube 30 to the fluid pump 24 whose opposite side is trifurcated into three distinct lines in the form of the flexible and deformable tubes 28A, 28B and 28C. These tubes extend through the associated pinch clamps 12A, 12B and 12C respectively. The tube 28A passing through pinch clamp 12A passes to a holding bag 102, the tube 28B passing through pinch clamp 12B passes to a saline bag 104 and the tube 28C passing through pinch clamp 12C passes to a collection reservoir 106.

In operation of the machine to cleanse blood from a wound site during a surgical procedure, a conventional suction tip 107 is moved through the wound site (not shown) by a surgical nurse to withdraw blood from the site and conventionally mix it with an anti-coagulant retained in an anti-coagulant bag 108. The mixture of blood and anti-coagulant are then received and temporarily retained within the collection reservoir 106. The outlet from the collection reservoir is, as mentioned previously, connected by the tube 28C, through pinch clamp 12C, to the fluid pump 24. Before the autotransfusion machine is operated, there is a supply of blood in the collection reservoir and there is further a supply of saline within the saline bag 104 which is connected to the fluid pump through the pinch clamp 12B and the tube 28B.

The initial cycle of the autotransfusion machine places pinch clamps 12A and 12B in closed positions and pinch clamp 12C in an open position. The separator bowl 20 is then rotated and the fluid pump 24 activated to pump blood from the collection reservoir 106 through pinch clamp 12C into the separator bowl until a predetermined level of red blood cells has accumulated within the separator bowl. The separator bowl is positioned adjacent to a conventional level detector (not seen) which electronically advises the machine when a predetermined level of red blood cells has accumulated within the separator bowl. During centrifugation, the undesirable elements of the blood mentioned previously are removed through the top of the bowl and transferred into the waste bag 100. When the level of red blood cells reaches the predetermined level, the drive motor 92 associated with the crankshaft 88 is activated moving the pinch clamps so that pinch clamps 12A and 12C become closed to occlude the flow of fluid through the associated tubes and pinch clamp 12B is opened. This allows saline from the saline bag 104 to be pumped into the separator bowl 20 to wash whatever remaining undesirable blood components exist in the red cells so that they can be transferred to the waste bag while the heavier and cleansed red blood cells settle to the bottom of the separator bowl. After the undesirable elements have been washed from the red blood cells, the fluid pump 24 is stopped and the centrifuge or separator bowl is stopped while pinch clamp 12B remains open. After a slight delay, the fluid pump is again activated in a reverse direction to pump the red cells in the separator bowl out of the bowl thereby creating a backflush of the saline remaining in the tube 28B between the saline bag 104 and the separator bowl 20. This backflush occurs for a short predetermined time until the red blood cells move just past the fluid pump. Thereafter the drive motor 92 is again activated, changing the condition of the pinch clamps so that pinch clamp 12B closes to prevent the red blood cells from being pumped into the saline bag and pinch clamp 12A opens allowing the clean red blood cells to be pumped to the holding bag 102. When all of the red cells have been transferred into the holding bag, the pump stops and the machine repositions itself to repeat the aforenoted cycle.

As will be appreciated, the autotransfusion machine 14 receives blood and its contaminants and through a cycle of opening and closing the pinch clamps 12 while selectively operating the separator bowl 20 and the fluid pump 24, ultimately effects a transfer of clean red cells into the holding bag 102 from where they can be transferred and used for transfusion or reinfusion.

In order to keep track of the position of each pinch clamp so that related information can be displayed on a display screen 110 (FIGS. 1 and 2), a monitor plate 112 (FIG. 5) having circumferentially spaced sensors 114 is mounted on the framework 116 of the machine adjacent to the crankshaft 44. A sensor wheel 118 is keyed to the crankshaft so as to rotate therewith and operatively communicate with the sensors 114 to advise the electronics in the machine of the angular position of the crankshaft and consequently the position of each of the pinch clamps 12.

It should be appreciated that the pinch clamps of the present invention are positively activated in both a pinching and non-pinching condition since the cam followers 38 associated with each pinch clamp are positively moved by the crankshaft 88, cam wheels 40 and cam tracks 42 thereby positively moving the associated pistons 36 and effecting a dependable and timely occlusion of the flow of fluid through the tubes 28 associated with the clamps. As will also be appreciated and as discussed previously, when a piston is moved upwardly into pinching relationship with an aligned tube, the pinch bar 74 will initially engage the tube but some of the piston rod 66 movement will be absorbed by the compression spring 68 to more slowly move the pinch bar into a finally occluding relationship with the tube. Such action minimizes damage to the tube while providing for a positive occlusion of the flow of fluid through the tube.

Although the present invention has been described with a certain degree of particularity, it is understood that the present disclosure has been made by way of example, and changes in detail or structure may be made without departing from the spirit of the invention as defined in the appended claims.

We claim:

1. A clamp for occluding the flow of fluid through a deformable, flexible tube comprising in combination,
    a hollow clamp head having a channel therein in communication with the hollow interior of the clamp head, said channel adapted to removably receive said tube,
    a clamping element reciprocally positioned in said hollow interior of said clamp head and adapted to cooperate with said clamp head in selectively pinching said tube to occlude the flow of fluid through said tube, said clamping element having a cam follower,
    a cam track adapted to cooperate with said cam follower to positively reciprocate said clamping element within said clamp head, and
    drive means for moving said cam track to effect reciprocating movement of said clamping element.

2. The clamp of claim 1 wherein said cam track is disposed in a cam wheel which is adapted to be rotated by said drive means, and said cam track defines a closed loop in said cam wheel so as to positively guide said cam follower throughout complete revolutions of said cam wheel.

3. The clamp of claim 2 wherein said clamping element is elongated and said cam follower defines a lateral projection on said clamping element, said cam wheel being positioned adjacent to said clamping element so as to allow said cam follower to be operatively received in said cam track.

4. The clamp of claim 3 wherein said cam follower projects from opposite sides of said clamping element, and there is a cam wheel on opposite sides of said clamping element operatively associated with said cam follower through said cam track on each cam wheel.

5. The clamp of claim 4 wherein said clamping element includes a piston head and a piston rod operatively connected to said piston head, said piston rod supporting said cam follower.

6. The clamp of claim 5 wherein said cam follower is a pin extending laterally through said piston rod.

7. The clamp of claim 6 wherein said piston head is hollow and said piston rod is slidably disposed therein, and further including resilient means positioned in said hollow piston head to yieldingly resist sliding movement of said piston rod in said piston head.

8. The clamp of claim 5 wherein said hollow clamp head is elongated having an open end slidably receiving said clamping element and a closed end, said channel in said clamp head passing transversely of the length of said clamp head adjacent to said closed end so that said clamping element can selectively pinch said tube against said closed end of the clamp head.

9. The clamp of claim 2 wherein said can track defines a groove in said cam wheel.

10. A system for selectively occluding the flow of fluid through a plurality of deformable, flexible tubes comprising in combination:
    a plurality of side-by-side clamps each including a hollow clamp head with a transverse channel therethrough for receiving a tube, an associated elongated clamping element reciprocally mounted in said clamp head so as to cooperate with said clamp head in pinching said tube to occlude the flow of fluid therethrough, said clamping element including a cam follower extending transversely to the length of said clamping element and projecting laterally therefrom, and a drive system for reciprocating said clamping elements within the associated clamping heads, said drive system including a rotatable drive shaft and a plurality of cam wheels with opposite faces keyed to said drive shaft for unitary rotation therewith, said cam wheels having at least one cam track in a face thereof receiving a cam follower with each cam follower being operatively associated with at least one cam wheel, whereby rotation of said drive shaft effects reciprocal motion of said clamping elements in said clamp heads to selectively pinch said tubes to occlude the flow of fluid therethrough.

11. The system of claim 10 wherein each clamping element includes a piston head and a piston rod operatively connected to said piston head, said piston rod supporting an associated cam follower.

12. The system of claim 11 wherein said cam followers are pins extending laterally through an associated piston rod and are operatively engaged with two cam tracks.

13. The system of claim 12 wherein said piston heads are hollow and said piston rods are slidably disposed therein, and further including resilient means positioned in said hollow piston heads to yieldingly resist sliding movement of said piston rods in said piston heads.

14. The system of claim 13 wherein said hollow clamp heads are elongated having an open end slidably receiving an associated clamping element and a closed end, said channels in said clamp heads passing transversely of the length of said clamp heads adjacent to said closed end so that an associated clamping element can selectively pinch an associated tube against said closed end of the clamp head.

* * * * *